United States Patent
Barbe-Vicuna et al.

(10) Patent No.: US 6,338,722 B1
(45) Date of Patent: Jan. 15, 2002

(54) COMPRESSION HOSE, COMPRESSION PANTS AND ACCOMPANYING COMPRESSION PAD

(76) Inventors: Albina Maria Lucrezia Barbe-Vicuna, Willem ll Straat 68, Nl-5038 BJ Tilburg (NL); Thomas Eduard Barbe-Vicuna, Heyhoefpromenade 267, NL-5043 RE Tilburg (NL)

( * ) Notice: Subject to any disclaimer, the term of this patent is extended or adjusted under 35 U.S.C. 154(b) by 0 days.

(21) Appl. No.: 08/894,301
(22) PCT Filed: Feb. 16, 1996
(86) PCT No.: PCT/NL96/00074
§ 371 Date: Aug. 15, 1997
§ 102(e) Date: Aug. 15, 1997
(87) PCT Pub. No.: WO96/25131
PCT Pub. Date: Aug. 22, 1996

(30) Foreign Application Priority Data

Feb. 17, 1995 (NL) .............................................. 9500307

(51) Int. Cl.[7] .................................................. A61F 13/00
(52) U.S. Cl. .......................................... 602/62; 602/75
(58) Field of Search .............................. 602/2, 4, 5, 20, 602/21, 61, 60, 62, 75; 128/869, 874, 877, DIG. 19; 2/44, 45, 267, 268, 239

(56) References Cited

U.S. PATENT DOCUMENTS

| | | | |
|---|---|---|---|
| 3,000,378 A | | 9/1961 | Zieman |
| 3,889,494 A | * | 6/1975 | Patience et al. ........... 66/178 R |
| 4,172,456 A | * | 10/1979 | Zens ........................... 602/63 |
| 4,469,095 A | | 9/1984 | Herrera |
| 4,745,917 A | * | 5/1988 | Hasty et al. ................... 602/63 |
| 4,985,934 A | * | 1/1991 | Perry ........................ 602/2 X |
| 5,154,690 A | * | 10/1992 | Shiono ........................... 602/5 |
| 5,181,906 A | * | 1/1993 | Bauerfeind ............... 602/61 X |
| 5,290,218 A | * | 3/1994 | Kilbey ........................... 602/4 |
| 5,449,341 A | * | 9/1995 | Harris .......................... 602/63 |

FOREIGN PATENT DOCUMENTS

| | | |
|---|---|---|
| EP | 0 467 183 | 1/1992 |
| GB | 2 242 818 | 10/1991 |

OTHER PUBLICATIONS

CAMP catalog, 1994, p. 12.*
CAMP Catalog, 1994 page 2.*

* cited by examiner

*Primary Examiner*—Denise Pothier
(74) *Attorney, Agent, or Firm*—Gilberto M. Villacorta; Corinne M. Pouliquen; Katten Muchin Zavis

(57) ABSTRACT

A compression device for exerting pressure on an arm, shoulder, and/or trunk of a patient in need thereof (for example, a patient with hyperalgia or recovering from surgery in which the lymphatic system is affected), including an arm compression hose, a shoulder part for exerting pressure on the shoulder and trunk area, and a band-shaped fastening means for positioning the shoulder part and exerting pressure on the shoulder part. The arm compression hose exerts a pressure that decreases from a maximum pressure at the wrist or hand to a minimum pressure near the shoulder end of the arm, where the minimum pressure is approximately 70% of the maximum pressure. One or more lining pockets can be constructed on the inner lining of the compression device, where each lining pocket can hold one or more compression pads to increase tissue pressure in one or more body areas in need thereof. The compression pads each can have a shape that approximately conforms to the shape of the body part to which it is applied. The shoulder part can also have a shape that approximately conforms to the contour of the shoulder/trunk area to which it is applied. In addition, compression pants can be prepared with lining pockets for receiving compression pads. In one embodiment, compression pants include one or more donut-shaped pads or equivalents thereof that are placed in one or more lining pockets, each of which surrounds one or more osteoma openings.

1 Claim, 4 Drawing Sheets

COMPRESSION HOSE, COMPRESSION PANTS AND ACCOMPANYING COMPRESSION PAD

1. TECHNICAL FIELD

The present invention relates to a compression hose of elastic material for exerting tissue pressure on an arm of a patient, in which the compression hose comprises a shoulder part which partially covers the shoulder joint when in use, while fastening means for fastening the compression hose are provided on the shoulder part.

Such a compression hose is known in practice and is generally used to counteract oedema formation in an arm in an oedematous patient. For this purpose, the elastic material of the arm part has a predetermined compression value. The known compression hose is provided with a narrow shoulder part which is approximately 8 to 10 cm wide and serves to fasten a band of elastic material by means of which the compression hose, is fastened to the trunk of the patient.

The object of the compression hose according to the present invention, is to solve very specific and commonly occurring problems in a particular group of oncology patients to which until now, no solution had been found.

2. BACKGROUND ART

Surgery and radiotherapy are generally used in the treatment of cancer. In many cases a large part of the lymph nodes is removed from lymph areas situated near the tumour(s).

As a result of damage to the primary lymph drainage channels, for example, as may result from surgery and radiation treatment, a reduced lymph transportation capacity can occur in this case in the areas concerned, which produces so-called "relative lymphostasis", or the clinical oedema-free stage. In this stage, pathological changes, such as accumulations of fibrinoid material, already occur in the tissue. In lymphostasis or its manifestation—oedema—we see accumulations of plasma proteins in the tissue. Both in relative lymphostasis and in lymphostasis, these plasma proteins are responsible for the inflammatory stimulation which maintains a non-specific inflammatory reaction in the tissue, which is a characteristic tissue reaction in relative lymphostasis and lymphostasis.

On account of the above, the pain symptoms experienced post-operatively by oncology patients who have undergone mainly axillary and inguinal lymph gland dissection can be defined as chronic lymph circulation disturbances in which primarily painful congestion and inflammation occur, so-called hyperalgesia.

Hyperalgesia in the operated hemithorax (the half of the trunk) and the corresponding arm or in the operated lower half of the trunk and the corresponding leg generally occurs in the clinical oedema-free stage, both in intermittent reversible oedema and in slight to moderate oedema.

More severe forms of hyperalgesia occur in the case of malignant lymph oedema and with the occurrence of acute radiation reactions during radiation treatment. In an acute radiation reaction, due to hyperaemia caused by the heat effect, increased permeability of the capillary blood vessels to plasma proteins occurs. At the point where a painful protein-rich swelling already existed after the operation, a severe form of hyperalgesia occurs in the form of a stinging, burning feeling. In this context we could mention seroma formation, haematoma formation, infiltration, slow-healing wounds, infection and in general all situations in which post-operatively an increased concentration of plasma proteins is already present in the tissue.

The above symptoms are of a subchronic to chronic nature and can be readily overcome in particular following the use of manual lymph drainage (MLD). Manual lymph drainage is a special form of non-forcing massage. Manual lymph drainage promotes the reabsorption of (protein-rich) tissue fluid in blood and lymph capillaries and stimulates the motor function of the lymph vessels, with the result that the lymph transportation capacity increases and the symptoms decline or disappear. (Relative) lymphostasis in the above-mentioned areas is prevented or relieved here by increasing the tissue pressure from the outside.

The aetiology, pathogenesis and treatment of hyperalgesia, in this case by manual lymph drainage and compression therapy, constitutes an entirely new area within lymphology.

3. DISCLOSURE OF THE INVENTION

The object of the invention is to overcome the above-mentioned problems and indicate a solution by which the beneficial effects of manual lymph drainage in the supra-clavicular area, the armpit folds front and back, the shoulder area and/or the cranial trunk areas (anterior and posterior) in a patient are consolidated and/or increased.

This is achieved in the case of a compression hose according to the invention through the fact that the shoulder part is lengthened in such a way that when in use it extends past the h-line running vertically from the armpit to the shoulder line, and through the fact that the shoulder part is widened in such a way that when in use it covers at least an area on the trunk, which is at least bounded by a band-shaped fastening means running from the ipsilateral shoulder, around the front of the trunk to the contralateral side of the trunk in the area of the patient's waist, and around the back of the trunk to the ipsilateral shoulder, such that the band-shaped fastening means forms an acute angle relative to a g-line, which is defined as a horizontal line running between the armpits at the respective ipsilateral and contralateral sides of the trunk, and a boundary line running from the patient's armpit to the band-shaped fastening means, whereas the shoulder part exerts an approximately constant, adequate tissue pressure when in use.

A lengthened and widened shoulder part is known per se from GB-2242818. This British patent application describes protective garments, in particular a protective garment for keeping the shoulder joint warm. The known garment comprises various types of elastic material with a differing degrees of elasticity. The shoulder part thereof has undergone a special treatment, as a result of which it retains heat better.

The known protective garment with lengthened and widened shoulder part is entirely unsuitable for the object of the present invention, i.e. for the treatment of hyperalgesia, in this case for consolidating and increasing the beneficial effects of manual lymph drainage in the relevant abovementioned areas of the human body. The envisaged heat effect of the known garment in fact promotes the formation of oedema, and consequently of hyperalgesia. In addition, the known garment exerts an abruptly changing tissue pressure on the tissue, due to the use of a combination of materials with differing degrees of elasticity. On the other hand, the compression devices according to the present invention treats hyperalgesia by exerting an approximately constant pressure through the shoulder part thereof, whereas the remaining part comprises an arm compression hose which preferably exerts a gradually decreasing tissue pressure as the length of the arm compression hose is traversed from the distal (i.e., hand and/or wrist) to the proximal (i.e., the shoulder end of the arm) end.

In a further embodiment the shoulder part is made wider at the front and back of the trunk of the patient. In this embodiment the compression hose will slip little, if at all, after fastening, with the result that pressure is exerted on the tissue at the correct points.

In a further embodiment the shoulder part is slightly preshaped. The compression hose according to this embodiment can advantageously be adapted to the anatomical shape of the trunk area of the particular patient which runs between an h-line, a g-line, and the band shaped fastening device (mentioned above), as described further below, when this area of the patient and requires treatment.

In a further advantageous embodiment the compression hose is provided, at at least one place at the side next to the body, with a lining pocket for the accommodation of a compression pad, in order to increase the local tissue pressure. In this embodiment the tissue pressure can advantageously be increased further locally, in order to give optimum pain relief. The corresponding pressure change has a gradual course, viewed from distal to proximal, even when a compression pad according to the invention is used. This compression hose is suitable in particular for treating cases of severe hyperalgesia.

The present invention also relates to compression pants of elastic material provided with legs, which in use at least partially cover the upper legs of a patient.

In practice, such compression pants of elastic material are known, for example, cycle racing shorts.

The object of the invention is to make the known compression pants suitable for local consolidation and/or increasing of the beneficial effects of manual lymph drainage in the treatment of hyperalgesia in the area to be covered by the compression pants.

To this end, the compression pants according to the invention are characterized in that, at at least one place at the side next to the body, they are provided with a lining pocket for the accommodation of a compression pad, in order to increase the local tissue pressure.

The compression pants according to the invention make it possible also to exert an increased tissue pressure on congested or damaged lymph areas in, inter alia, the hip and/or abdomen area, the pubic area and/or the groin area of the patient.

The present invention also relates to a compression pad for use in the compression hose and/or the compression pants, in which the shape of the compression pad is adapted to the anatomical shape of the place on the body of the patient on which the compression pad exerts pressure when in use. Such a compression pad provides a non-forcing pressure from the outside on the congested and painful area concerned, with the result that the tissue pressure locally rises further, and the effect of the MLD is consolidated and/or increased, and recurrence of hyperalgesia is counteracted when the MLD has ended.

BRIEF DESCRIPTION OF THE DRAWINGS

The invention will be explained in greater detail with reference to the figures, in which.

MODES FOR CARRYING OUT OF THE INVENTION

Figure 1:
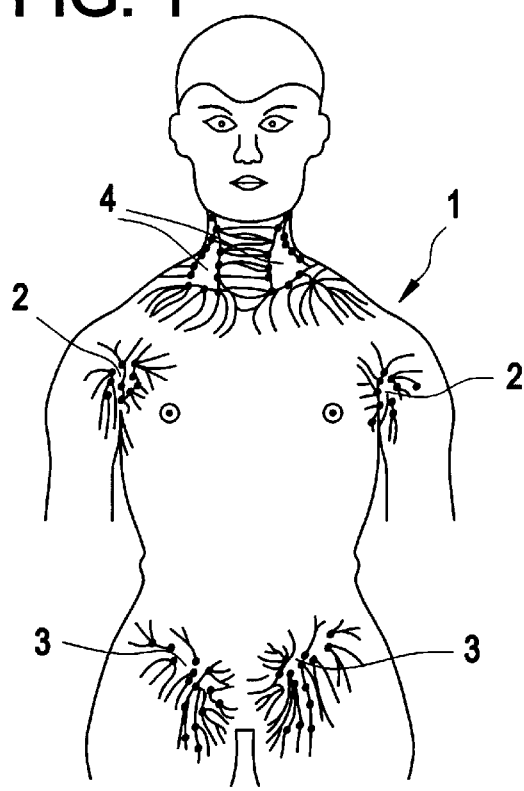
FIG. 1 shows a part of the human body, in which a number of lymph drainage areas are indicated.

FIG. 1 shows a part of a human body 1 at the front, indicating a number of lymph drainage areas and lymph nodes 2 to 4, on which the tissue pressure can be increased by means of the compression hose and/or the compression pants according to the invention. The axillary lymph glands near the armpits are indicated by reference number 2. The lymph areas around the groins are indicated by reference number 3. Reference number 4 indicates the supraclavicular lymph areas and the neck lymph areas. Lymph gland dissection in the lymph drainage areas shown can be the cause of hyperalgesia occurring in the operated hemithorax and the corresponding arm, and in the lower operated trunk area and the corresponding leg.

Figure 2:
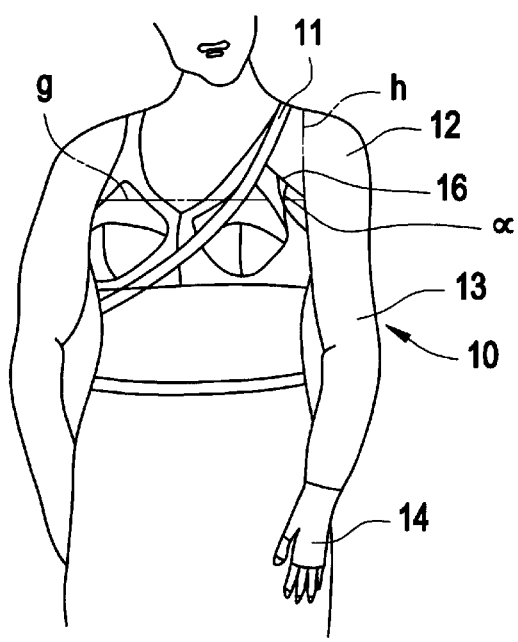
FIG. 2 shows a preferred embodiment of a compression hose according to the present invention.

FIG. 2 shows a preferred embodiment of an arm compression hose 10 according to the present invention.

In the preferred embodiment, arm compression hose 10 comprises band-shaped fastening means 11, which is fitted on shoulder part 12. In an alternative embodiment, arm compression hose 10 is provided with fastening means for fastening the arm compression hose on a garment, such as a brassiere (not shown). Arm compression hose 10 also comprises an arm part 13, and can be provided optionally with a hand part 14.

Depending on the symptoms, the shoulder part 12 can be widened or lengthened in the direction of certain painful areas on the trunk of the patient. When axillary lymph nodes are removed in the area 2 (see FIG. 1), the shoulder part 12 can be widened correspondingly in the direction of the armpit/armpit folds of the patient. The shoulder part 12 is widened in such a way that when in use it covers at least an area on the trunk which for the rest is bounded by band-shaped fastening means 11 and a boundary line 16, running from the patient's armpit to band-shaped fastening means 11. The boundary line 16 is preferably situated essentially at an angle $\alpha$ of between $-45$ and $+45$ degrees with the g-line running horizontally between the two armpits. More preferably, the width of the shoulder part of the compression device according to the invention is $\geq 10$ cm.

When pain is being experienced in the area 4 (see FIG. 1) the shoulder part 12 can be lengthened accordingly in the direction of the neck of the patient. The shoulder part is then lengthened according to the invention in such a way that when in use it extends past the h-line, which runs vertically from the armpit to the shoulder line. In a preferred embodiment the shoulder part 12 extends at the most to the curve of the neck, with the result that irritation from the fastening means 11 in the patient's neck during wearing of the compression hose 10 is effectively prevented.

The shoulder part 12 can also be slightly preshaped, so that it can be adapted in the optimum manner to the anatomical shape of the part of the trunk running between the h-line and g-line, and band-shaped fastening means 11 in the patient concerned.

Although FIG. 2 shows only a widening at the front, it will automatically be clear to a person skilled in the art that the widening can also be applied at the back, in order to exert pressure on the cranial trunk areas.

The arm compression hose 10 is made of elastic material with a predetermined compression value. Said compression value is adapted to the desired treatment. In practice, the compression values are broken down into classes. An example of a classification commonly used in Germany is given below.

Class 1: 20–30 mm Hg
Class 2: 30–40 mm Hg
Class 3: 40–50 mm Hg

All compression values from classes 1, 2 and 3 are easily usable for medical treatments.

The compression value of the present arm compression hose falls mainly in classes 2 and 3. The compression value thereby decreases from the wrist in the direction of the g-line. For example, assuming that the wrist compression value is 100%, then the compression value is approximately 70% near the g-line. The arm compression hose according to the invention preferably has a gradual change in compression value, from 100% of the maximum pressure at the wrist and/or hand, to approximately 70% of the maximum pressure at the shoulder end of the arm near the g-line, whereas the compression value of the shoulder part in the preferred embodiment is essentially equal to the compression value near the g-line (i.e., approximately 70% of the maximum pressure). The compression in the lymph areas around the shoulder in this case is brought about partly by adapting the shoulder part 12 to the anatomical shape of the particular area of the patient's body and by pulling the band-shaped fastening means 11 sufficiently taut.

Shoulder part 12 is preferably widened both at the front and the back of the patient's trunk. The advantage of this is that the arm compression hose 10 will slip little, if at all, when in use, with the result that it is ensured that pressure is always applied in the correct place to the tissue concerned.

The arm compression device according to the present invention can be used in the following indication areas:
1) hyperalgesia in general
2) hyperalgesia in the case of acute radiation reactions
3) palliative treatment of malignant lymph oedema
4) oedema formation
5) gland dissection
6) seroma formation
7) haematoma formation
8) infiltration
9) pasty fibrosis (soft fibrosing)
10) fibrosis
11) painful scars (adhesions, dehiscence, redness, itching), not only in the operated hemithorax and the corresponding arm, but also in the operated half of the lower trunk and the corresponding leg.

Figure 3:
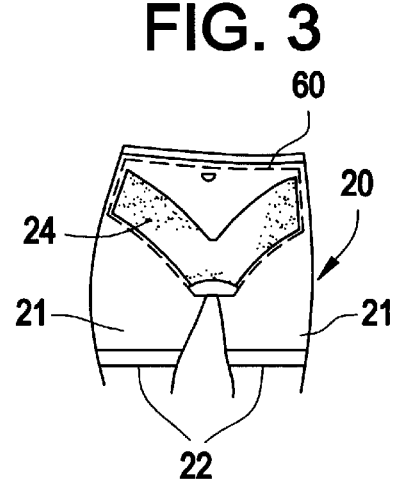
FIG. 3 shows a first preferred embodiment of compression pants according to the invention.

FIG. 3 shows a first preferred embodiment of compression pants 20 according to the invention. Compression pants 20 have legs 21, each of which is provided with a broad, supple cuff 22, preferably measuring 3 to 5 cm, in order to prevent pinching. Compression pants 20 are made of elastic material with a preferably essentially constant compression value of class 1 to 3. In the preferred embodiment shown, compression pants 20 are pre-eminently suitable for exerting pressure on the abdomen/hip area, the pubic area, the groin area and parts of the thighs. Depending on requirements, the legs of the compression pants can extend over the entire leg, including the foot, of the patient (not shown).

The compression pants according to the invention are provided at at least one point at the side next to the body with a lining pocket (not shown) for the accommodation of a compression pad, in order to increase the tissue pressure. This lining pocket is preferably made of thin, stretch material with few seams, and can either be knitted or sewn into the pants. The lining pocket itself may be divided into various compartments, in which several compression pads can be inserted. The use of such a compression pad provides for non-forcing pressure from the outside on an indication area, with the result that the tissue pressure rises further. It can be pointed out that the compression pants according to the invention can also be used in the indication areas 1 to 11 listed above as regards the part of the body which is covered by the compression pants when they are in use, which is in particular the hip/abdomen area, the pubic area, the groin area, the legs and the feet.

In the preferred embodiment shown, compression pants 20 are provided with a v-shaped compression pad 24 placed inside lining pocket 60 for the pubic area and the lower abdomen/groin area.

Figure 4:
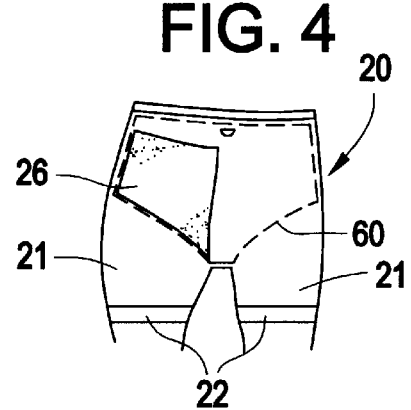
FIG. 4 shows a second preferred embodiment of compression pants according to the invention.
Figure 5:
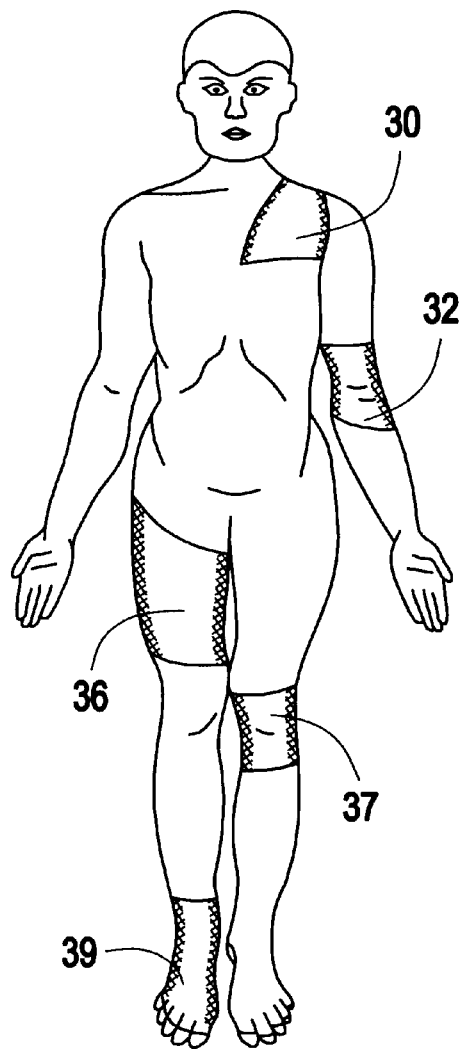
FIGS. 5 to 14 show exemplary embodiments of compression pads for use with the compression hose and/or the compression pants according to the invention.
Figure 6:
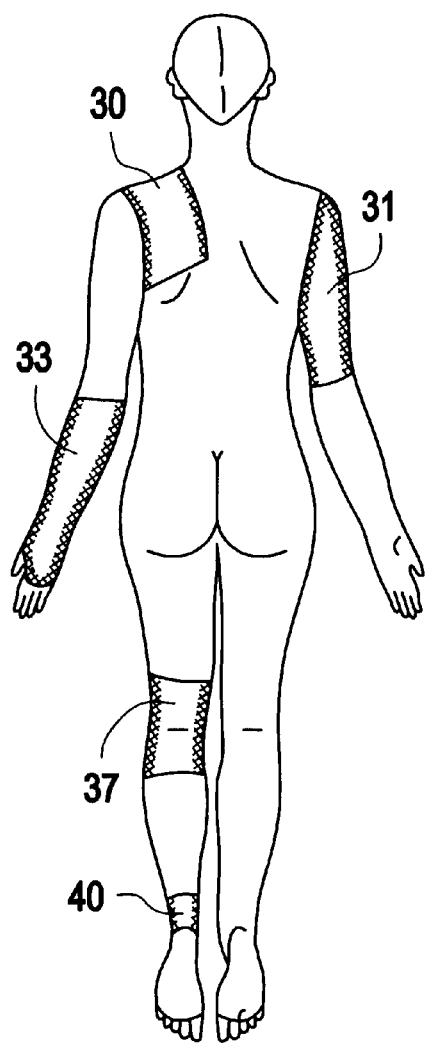
Figure 7:
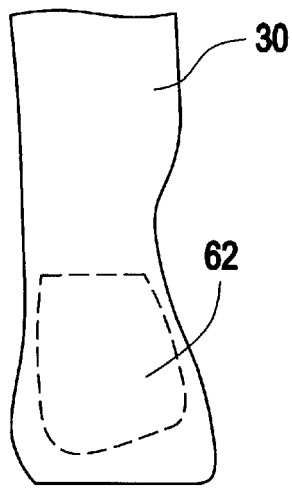
Figure 8:
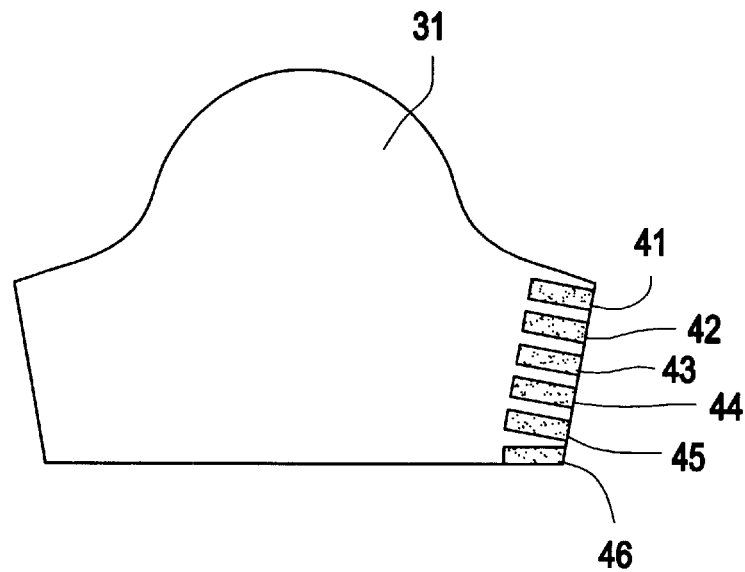
Figure 9:
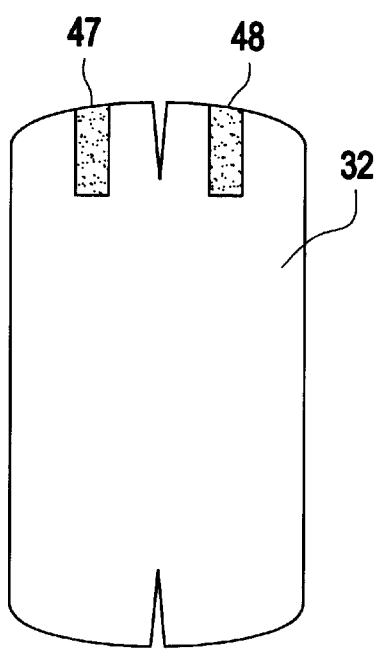
Figure 10:
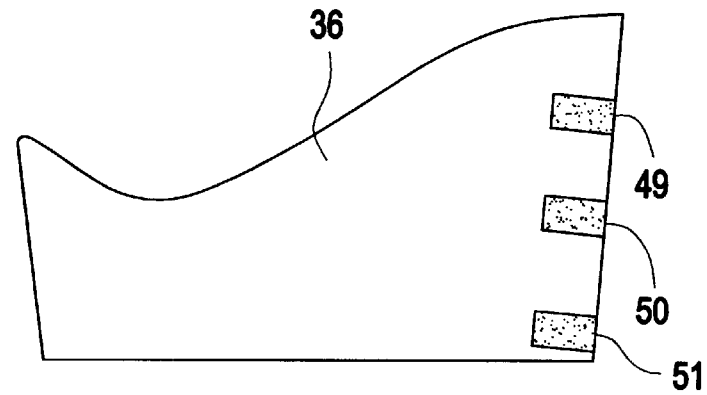
Figure 11:
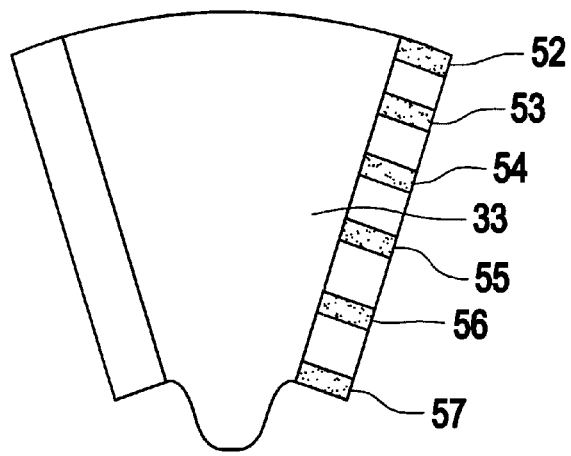
Figure 12:
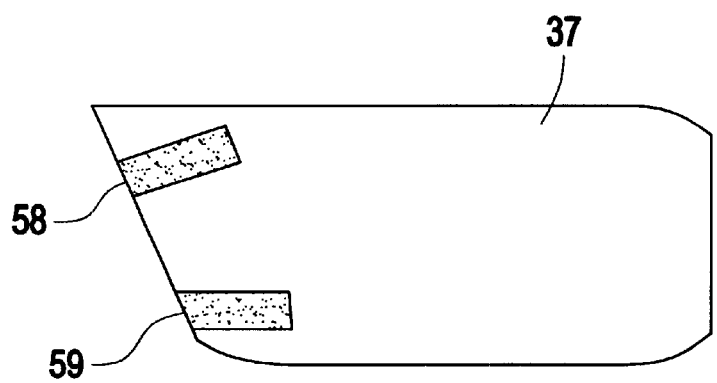
Figure 13:
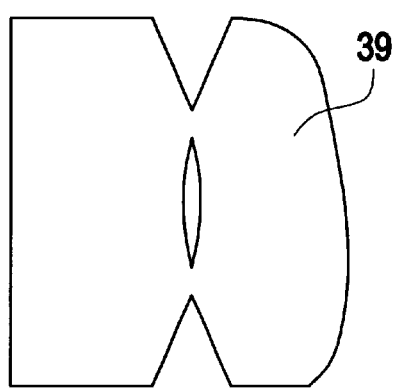
Figure 14:
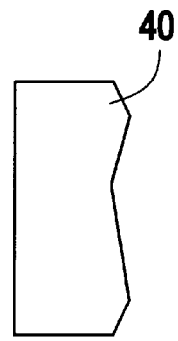

FIG. 4 shows a second preferred embodiment of compression pants according to the invention. Compression pants 20 are provided with compression pad 26 for the hip/abdomen area of the right side of the patient by use of lining pocket 60. Similarly, or in addition to, a compression pad may be inserted into pocket 60 for the left side of the patient, or a single compression pad may entirely fill lining pocket 60.

In order to achieve optimum freedom of movement for the patient, separate compression pads will generally be provided for the legs. To this end, the compression pants according to the invention are preferably provided with one or more corresponding separate lining pockets for the accommodation of the respective one or more compression pads.

It can also be pointed out that compression pads 24 and 26 are shown only at the front, but it will be clear that they can also extend to the rear of the trunk where necessary.

It can also be pointed out that the compression pants can be made suitable for osteoma patients by providing both the compression pants and the compression pads to be accommodated therein with openings which are adapted to the shape and location of the one or more osteomas concerned including the use of a donut shaped pad or equivalent thereof (e.g., two or more partial donut shaped pads that, collectively, define a donut shape when placed appropriately end-to-end within a lining pocket therefore) placed about an osteoma opening/outlet.

A compression pad is preferably made of resilient material about 0.5–1 cm thick, such as foam rubber, which is made with the edges flattened off or bevelled, and which is clad with, for example, a thin material with few or no seams. The delicate and careful treatment principle of manual lymph drainage is carried further in the finishing of this compression pad, which generally has a large surface area. Each thick or hard seam in the surface to be treated has a counterproductive effect and is therefore subject to high standards, in order to achieve the desired objective.

The foam rubber of the compression pad in some cases is smooth at least on one surface, and in other cases is provided with small grooves on said surface, as a result of which individual compression cushions are produced. It is also possible to use individual cushions of resilient material which, after fastening on said surface of the compression pad, can exert additional pressure on concavities in the area to be treated. These compression cushions are particularly suitable for treatment after gland dissection and/or in the case of scars, where the latter can fully or partially fill up the tissue cavity which has sometimes occurred.

The compression pad and the individual cushion can be made to measure and are accommodated in said lining pockets.

The shape and dimensions of each compression pad are adapted to the anatomical shape and dimensions of the place on the body where the compression pad concerned is to exert pressure.

In order to increase local tissue pressure in the supraclavicular area, the shoulder area and the cranial trunk area, compression hose 10 can also be provided with one or more lining pockets for the accommodation of compression pads and/or compression cushions of the type mentioned above.

FIGS. 5 to 14 show further exemplary embodiments of compression pads for use in the case of the compression hose and/or the compression pants according to the invention.

In these figures:
30. is an anatomically shaped compression pad for adequate treatment of the supraclavicular area, the shoulder area and the cranial trunk area;
31. is an anatomically shaped compression pad for treatment of the upper arm;
32. is an anatomically shaped compression pad for treatment of the elbow area;
33. is an anatomically shaped compression pad for treatment of the lower arm and back of the hand;
36. is an anatomically shaped compression pad for treatment of the thigh or upper leg;
37. is an anatomically shaped compression pad for treatment of the knee and back of the knee;
39. is an anatomically shaped compression pad for treatment of foot and ankle;
40. is an anatomically shaped compression pad for treatment of the ankle.

Compression pads/cushions 30 to 33 are suitable for use in the arm compression hose and/or compression device according to the invention. Compression pads 36 and 37, 39 and 40 are suitable for use in the compression pants according to the invention. When in use, a compression pad is essentially covered by the compression hose or pants. With respect to FIG. 7, lining pocket 62 is shown for receiving one or more compression pads/cushions.

In general, when compression pads are used in conjunction with an arm compression hose, a compression device, and/or compression pants according to the invention, the total pressure on the arm or the leg is greater distally than proximally, in order to make the lymph stream flow away to the proximal discharge areas in the best way possible.

If desired, a compression panty hose can be worn over the short-legged compression pants, the compression value of said panty hose being selected in such a way that the compression value increases from the thigh towards the foot. In this way shifting of the symptoms to the lower leg is prevented.

It can be pointed out that all compression pads can be provided with one or more corresponding compression cushions. All compression pads can be produced both as left-side and as right-side models. Each compression pad can be provided with Velcro (see fastening elements 41–59 in FIGS. 8 to 12) or other known fastening means, in order to hold the compression pad in position.

It will automatically be clear to a person skilled in the art that the compression pads can be adapted both in length and in width to the size of the body area to be treated, without departing from the idea of the invention. For example, compression pad 36 can cover only the inner half of the thigh if the patient's symptoms are limited to that area.

What is claimed is:

1. A method of treating the symptoms of hyperalgesia comprising:
   selecting a compression device comprising:
      an elastic material, where said elastic material exerts pressure on at least a portion of an arm, a shoulder, and a trunk of a patient in need thereof, and where said elastic material further comprises an inner side and an outer side, where:
      the arm comprises a wrist, an elbow, and a shoulder end;
      the trunk comprises a front, a back, a side ipsilateral to the arm, a side contralateral to the arm, a waist, and respective ipsilateral and contralateral arm pits; said elastic material further comprising:
         an arm compression hose for exerting pressure on at least a portion of the arm, where the arm compression hose is positionable to cover at least a portion of the arm, is sized and configured to extend from the wrist to the shoulder end, and wherein the pressure gradually decreases from a maximum pressure at the wrist to a minimum pressure near the shoulder end;
         a shoulder part for exerting pressure on at least a portion of the shoulder and the trunk; and
         a fastening means fitted on the shoulder part, extending diagonally from the shoulder part, and wrapping around the patient from the side of the trunk ipsilateral to the arm to the side contralateral to the arm;
   applying and fitting the compression device to the body of the patient, comprising:
      selecting the arm compression hose elastic material to provide:
         a maximum compression value at the wrist from about 20 mm Hg to about 50 mm Hg; and
         a minimum compression value at the shoulder end of approximately 70 percent of the maximum compression value; and
      tightening the fastening means so that the shoulder part exerts a tissue pressure of approximately 70 percent of the maximum compression value.

* * * * *